(12) United States Patent
Foster

(10) Patent No.: US 7,434,788 B2
(45) Date of Patent: Oct. 14, 2008

(54) PEST DETERRENT FENCE

(76) Inventor: Mark Foster, 1659 Blair Avenue, Victoria, British Columbia (CA) V8N 1M6

( * ) Notice: Subject to any disclaimer, the term of this patent is extended or adjusted under 35 U.S.C. 154(b) by 0 days.

(21) Appl. No.: 11/684,537

(22) Filed: Mar. 9, 2007

(65) Prior Publication Data

US 2008/0217597 A1 Sep. 11, 2008

(51) Int. Cl.
*A01M 1/24* (2006.01)
(52) U.S. Cl. ............... 256/10; 256/1; 256/11; 47/33; 43/98; 43/124
(58) Field of Classification Search ........ 256/1, 256/10, 11; 47/33; 43/98, 112, 121, 124
See application file for complete search history.

(56) References Cited

U.S. PATENT DOCUMENTS

| | | | | |
|---|---|---|---|---|
| 4,118,752 A | * | 10/1978 | Iguchi | 256/10 |
| 4,706,941 A | * | 11/1987 | Sherdan | 256/10 |
| 4,756,116 A | * | 7/1988 | Cutter | 43/112 |
| 4,839,984 A | * | 6/1989 | Saunders et al. | 43/112 |
| 5,557,879 A | * | 9/1996 | Ott | 43/112 |
| 5,967,084 A | * | 10/1999 | Klemantaski | 43/112 |
| 6,036,175 A | * | 3/2000 | Harper | 256/10 |
| 6,712,339 B1 | * | 3/2004 | Smith | 256/10 |
| 2005/0132635 A1 | * | 6/2005 | Riddell | 43/98 |

FOREIGN PATENT DOCUMENTS

DE 33 03 077 * 1/1983

* cited by examiner

*Primary Examiner*—Michael P Ferguson
(74) *Attorney, Agent, or Firm*—Gordon Thomson

(57) ABSTRACT

A pest deterrent fence is used to deter slugs and snails and similar animals from gaining access to gardens. The fence comprises vertically oriented first and second conductive surfaces that are generally metallic mesh. The conductive surfaces separated by a polyvinylchloride non-polar dielectric. The dielectric is "T" shaped and is dimensioned such that it prevents moisture from connecting the first and second conductive surfaces by promoting beading and dripping.

5 Claims, 3 Drawing Sheets

PEST DETERRENT FENCE

FIELD OF THE INVENTION

This invention generally relates to fences carrying an electrical current to deter or repel the movement of animals; and, vermin destroying apparatus such as a structure which repels or deters the movement of animal life. Specifically, this invention relates to a pest deterrent fence.

BACKGROUND OF THE INVENTION

Snails and slugs are well known garden pests. One way of dissuading their encroachment into gardens is to set an electrified fence in their path. There are many such devices in the known art such as that disclosed in U.S. Pat. No. 4,756,116 "Snail Barrier" issued to Cutter on Jun. 12, 1998. This type of fence generally comprises a first and second conducting surfaces separated by a non-conducting surface having a width less than the length of the animal. The animal attempts to cross the non-conducting surface and contacts both conducting surfaces causing an electrical current to flow through the animal. This deters the animal from further progress. A common problem associated with this type of fencing apparatus is that moisture in the form of rain or dew is able to create a current pathway across the non-conducting surface by wetting the entire non-conducting surface. This renders the barrier ineffective at a time when these animals are most active, that is, in moist conditions. As well, since the fence is effectively shorted, a battery power source will become quickly depleted.

Therefore there is a need for a pest deterrent fence that is able to function in high moisture environments and resist wetting of the non-conductive surface of such a fence.

SUMMARY OF THE INVENTION

The invention comprises a pest deterrent fence comprising a first conductive surface having a first voltage potential; and, a second conductive surface having a second voltage potential. The second conductive surface is adjacent to and above said first conductive surface in a co-planar relationship. The first voltage potential is higher than the second voltage potential. Between the two conductive surfaces is a non-conductive separating strip acting as a dielectric. The dielectric has a top horizontal surface having a width, a vertical surface having a thickness and a bottom horizontal surface. The dielectric is comprised of polymer material that is substantially non-polar so that it has a low surface energy.

The first conductive surface and the second conductive surface comprise a metallic mesh surface. In one embodiment of the invention the metallic mesh surface is a wire screen surface.

In another embodiment of the invention the difference between the first voltage potential and the second voltage potential is sufficient to create a deterrent voltage flow through the pest when it is in simultaneous contact with the first and second conductive surfaces.

In the preferred embodiment of the intention the width of the top horizontal surface is sufficiently wide to promote the self attraction and beading of water until the mass of the drop formed in sufficiently large to overcome the surface tension binding the drop to the top horizontal surface causing the drop to fall.

The dielectric further comprises a continuous strip of non-polar polymeric material. In one embodiment of the invention the dielectric strip is in the shape of a "T" having a leg and a first and second arm having inside surfaces. The leg of the "T" forms the dielectric and the inside surfaces the first and second arms form the top and bottom bonding surfaces for the top and bottom conductive surfaces respectively. The top and bottom conductive surfaces are joined to the top and bottom bonding surfaces respectively by adhesive means.

In another embodiment of the invention the top and bottom conductive surfaces are joined to the top and bottom bonding surfaces respectively by thermal bonding means.

The first and second conducting surfaces may be connected to an external power source in one embodiment of the invention. In another embodiment of the invention the first and second conductive surfaces are comprises of elements in the electro-chemical series sufficiently spaced apart on the periodic table to generate a current when in contact with each other.

OBJECTS AND ADVANTAGES

It is an object of the invention to overcome the deficiencies noted in the prior art.

It is a further object of the invention to provide a pest deterrent fence which is able to operate effectively in wet climates.

It is another object of the invention to provide a pest deterrent fence that does not short out in wet weather.

It is still a further object of the invention to provide a pest deterrent fence that promotes moisture beading and falling from the dielectric so as to avoid wetting the dielectric and shorting.

Still further objects and advantages of our invention will become apparent from a consideration of the following diagrams and detailed description.

DETAILED DESCRIPTION

Figure 1:
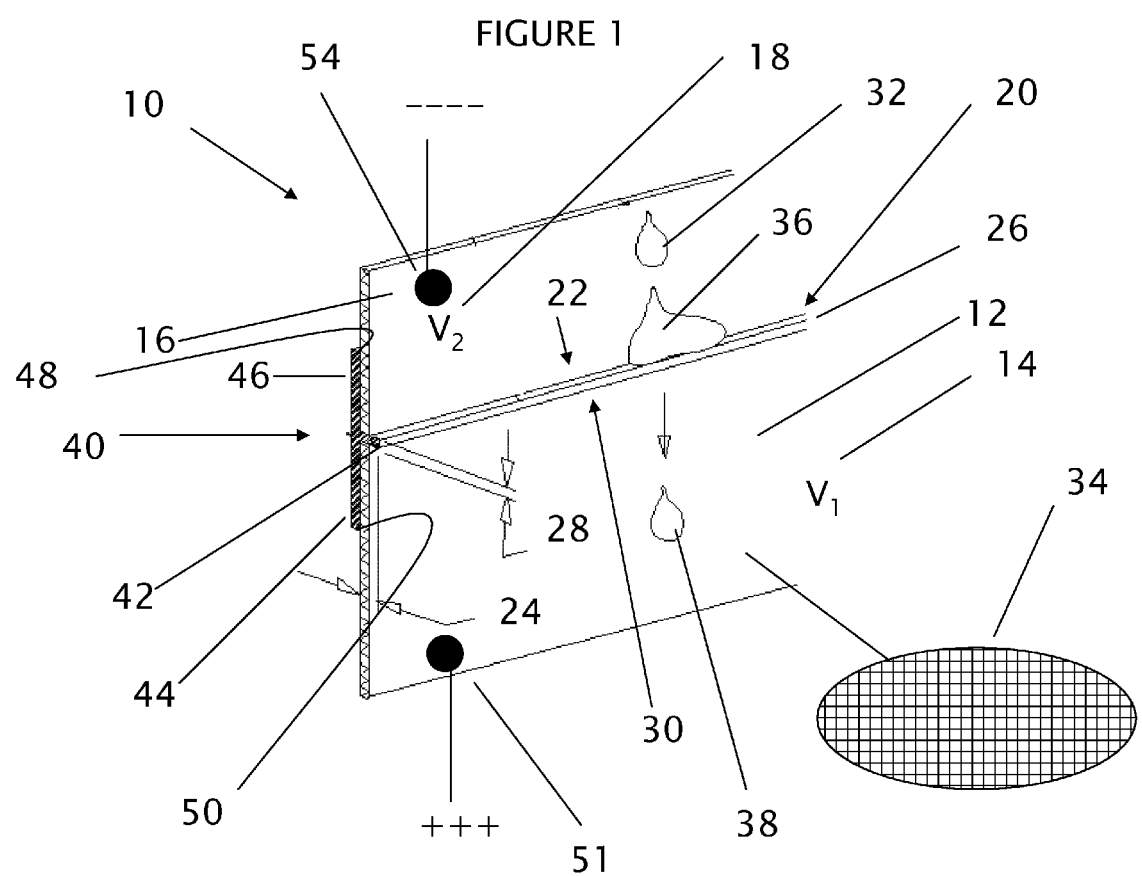
FIG. 1 is a view of one embodiment of the invention.

Referring to FIG. 1, my invention (10) is a pest deterrent fence to keep snails, slugs, worms and similar garden pests away from plants. Problems associated with previous known deterrent fences of this type include the wetting of the dielectric between conducting surfaces to such an extend that there is a current rack between them. This results in the same voltage on both sides of the dielectric and renders the fence ineffective in wet climates or other areas with heavy humidity and dew. It also results in excessive power use and battery depletion. Through much experimentation in the wet climates of Vancouver Island, I have discovered that a certain type and configuration of dielectric resists wetting and causes excessive moisture to bead and drop from the dielectric of my invention without contacting both sides of the dielectric.

My invention comprises a first conductive surface (12) having a first voltage potential $V_1$ (14) and a second conductive surface (16) having a second voltage potential $V_2$ (18). The second conductive surface (16) is adjacent to and above said first conductive surface (12) in a co-planar relationship. $V_1$ is greater than $V_2$ so that when a slug or snail or similar type of pest is in contact with both the first and second surfaces simultaneously the creature receives a shock that deters it from proceeding or causes it to fall off of the fence. The amount of current necessary to shock the creature is well known in the art of pest deterrence and is relatively small. The different in magnitude between the first voltage potential and the second voltage potential must be sufficiently small so that the current will not arc or track across the dielectric even if it is wet or dirty. However the different in magnitude between the first voltage potential and the second voltage potential must be sufficiently great to create a deterrent current flow through the pest when the pest is in simultaneous contact with the first and second conductive surfaces.

Separating the first and second conductive surfaces is a non-conductive separating strip (20). The non-conductive separating strip acts as a dielectric.

The dielectric (20) comprises a top horizontal surface (22) having a width (24). Perpendicular to the top horizontal surface and depending from it is a vertical surface (26) having a thickness (28). There is also a bottom horizontal surface (30) parallel to the top horizontal surface (22) having the same width (24).

The bottom (12) and top (16) conductive surfaces are illustrated in FIG. 1 as a solid plane but they may also take the form of a metallic mesh surface such as a wire screen surface (34).

The dielectric (20) is further comprised of polymer material that is substantially non-polar or hydrophobic. In a preferred embodiment of the invention the polymer material is polyvinylchloride having a suitable hardness and resistance to cold and hot weather. The surfaces of the non-polar dielectric repel the polar water molecules causing them to form drops (32) rather than wetting over a larger surface area. Since the dielectric has a low surface energy, the drops are not allowed to spread out on its surface and so there is less tendency for the water to flow from the top surface (22) around the vertical surface (26) and across the bottom horizontal surface (30) thereby creating a current track from the bottom conductive surface (12) and the top conductive surface (16). The width (24) of the top horizontal surface (22) is sufficiently wide to promote the self attraction and beading of water on the top horizontal surface until the mass of the drop formed (36) is sufficiently large to overcome the surface tension binding the drop to the top horizontal surface causing the drop to fall (38).

Figure 2:
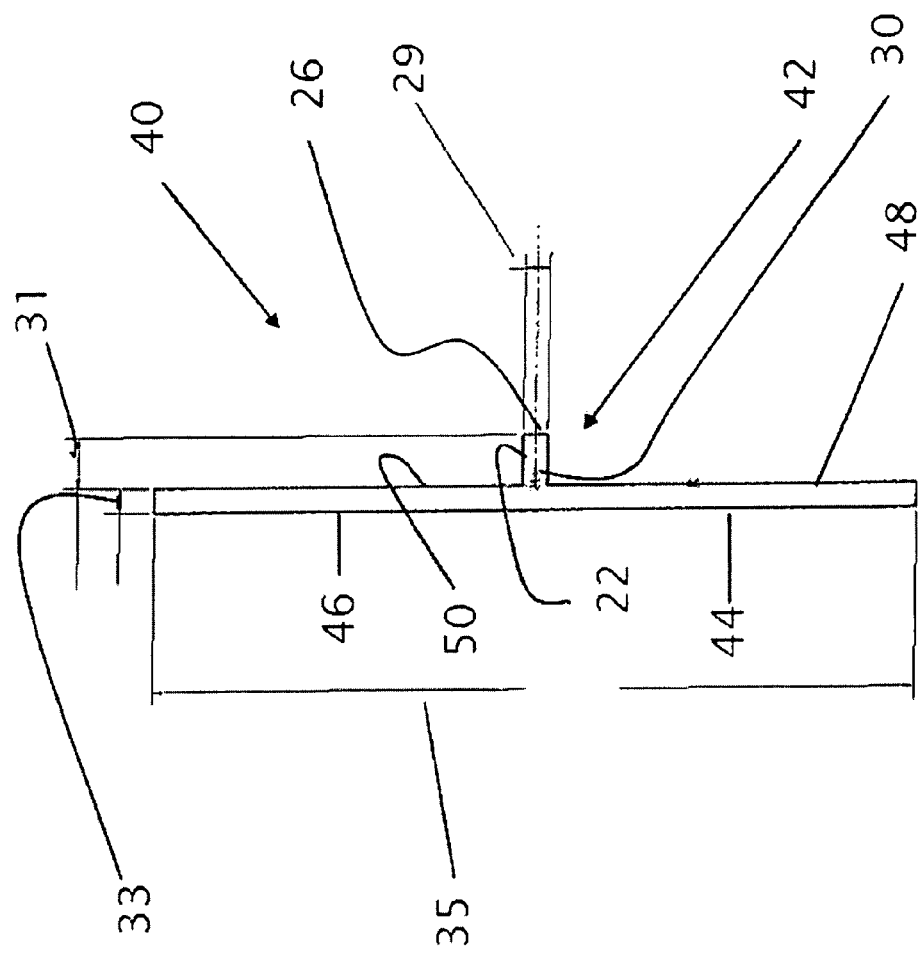
FIG. 2 is a view of one embodiment of the dielectric of the invention.

As FIG. 1 and FIG. 2 illustrate the continuous strip of non-polar polymeric material is in the shape of a "T" (40). The "T" has a leg (42) and a first (44) and second (46) arm having inside surfaces (48) and (50) respectively. The leg (42) of the "T" forms the dielectric and the inside surfaces (48) and (50) of the first and second arms form the top and bottom bonding surfaces for the top and bottom conductive surfaces respectively. The top and bottom conductive surfaces may be joined to the top and bottom bonding surfaces respectively by chemical adhesive means or by thermal adhesive means. In a preferred embodiment of the invention and as shown in FIG. 2, the thickness (29) of the dielectric is 0.635 mm; the depth of the dielectric (31) is 1.35 mm; the thickness (33) of the first and second legs (44 & 46) is 0.635 mm and the height (35) of the combined first and second legs is 19.5 mm.

The bottom conductive surface has a large area than the top conductive surface.

The first and second conductive surfaces are connected between the positive (51) and negative (54) terminals of an external power source so as to create a voltage potential between them. In one embodiment of the invention, the external power source is a direct current power source such as a battery. In another embodiment of the invention the battery is charged by a source of alternating current through a charging transformer. In still another embodiment of the invention the battery is charged by solar means. In one embodiment of the invention the first and second conductive surfaces are comprised of materials capable of forming an electrochemical cell and generating an electromotive force sufficient to deter a pest when in contact with the first and second conductive surfaces simultaneously. Two such materials can be copper and zinc. Other materials in the electrochemical series of elements can be used.

Figure 3:
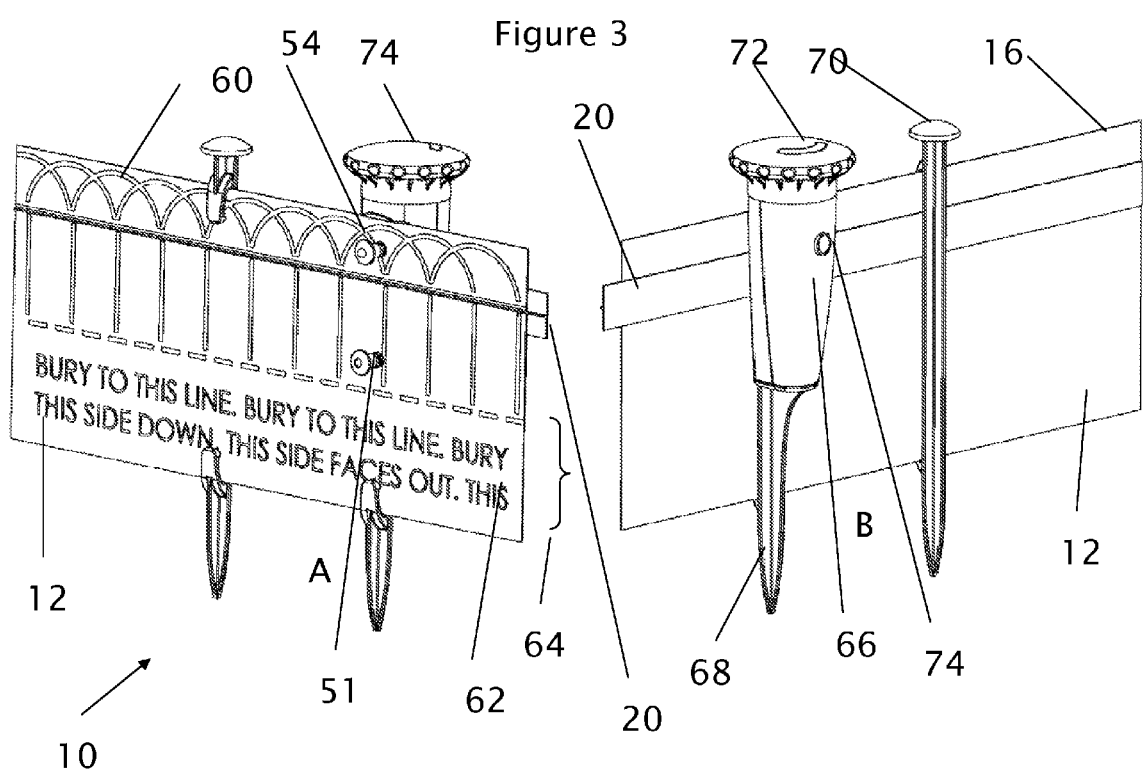
FIG. 3 is a view of one embodiment of a pest deterrent fence comprising one embodiment of the dielectric of the invention.

Referring to FIG. 3, the fence of my inventions (10) is continuous around an area of plant life to be protected so the dielectric further comprises a continuous strip (20) of non-polar polymeric material that will be as long as the fence. For example, the fence may be circular around a patch of flowers or rectangular around a garden bed. The fence is shown in a front view (A) and a rear view (B) and comprises a top (16) and a bottom conductive surface (12) separated by the dielectric strip (20). View A shows the front surface of the fence having a decorative finish (60) which in this embodiment is a fence design. View A also shows text instructions (62) to an operator as to how far to bury the bottom portion (64) in the ground. The invention is well suited to form kits that can be prepared for retail sales. The kits will comprise a suitable length of fence (10), at least one container (66) for containing a power source that is able to be staked into the ground by a stake (68), and a suitable number of fence support stakes (70). The fence may be decorated with a variety of pleasing designs. The invention is also well suited to the retail sale of spare parts for extending the fences such as rolls of fence (10) and additional power source containers (66) and fence support stakes (70). In this embodiment the power source is a battery stored within the container (66) having a battery life indicator (72) on the top of a container closure (74). The container (66) comprises a first (51) and second (54) electrical connectors which are adapted to pierce the fence at a suitable location. The container in this embodiment of the invention includes an on/off switch (74).

Although the description above contains much specificity, these should not be construed as limiting the scope of the invention but as merely providing illustrations of some of the presently preferred embodiments of this invention. Thus the scope of the invention should be determined by the appended claims and their legal equivalents.

What is claimed is:

1. A pest deterrent fence comprising:
   a. a first conductive surface having a first voltage potential comprising a first panel having a width;
   b. a second conductive surface having a second voltage potential comprising a second panel having said width;
      i. wherein, said second conductive surface is adjacent to and above said first conductive surface in a co-planar relationship;
      ii. and wherein, said first voltage potential is higher than said second voltage potential; and,
   c. a continuous separating strip of non-conducting, non-polar and hydrophilic material having a low surface energy, wherein said separating strip comprises a T-shaped dielectric having a leg disposed between and protruding from the first and second conductive surfaces and first and second arms perpendicular to said leg forming said T-shape and abutting said first and second conductive surfaces, said leg having:
      i. a top horizontal surface having a width sufficiently wider than said width of said first and second conductive surfaces to promote the attraction and beading of water until the mass of a drop of water is sufficiently large to overcome the surface tension binding the drop to said top horizontal surface causing the drop to fall clear of said first and second conductive surfaces;

ii. a vertical surface having a thickness and depending from said top horizontal surface and perpendicular thereto; and, iii. a bottom horizontal surface parallel to said top horizontal surface having said width;

iv. wherein said dielectric is adapted to prevent moisture from connecting the first and second conductive surfaces.

2. The fence of claim 1 wherein the dielectric further comprises polyvinylchloride.

3. The fence of claim 1 wherein said inside surfaces of said first and second arms form top and bottom bonding surfaces for the second and first conductive surfaces respectively.

4. A pest deterrent fence comprising:
a. a first conductive surface having a first voltage potential comprising a first panel having a width;
b. a second conductive surface having a second voltage potential comprising a second panel having said width;
  i. wherein, said second conductive surface is adjacent to and above said first conductive surface in a co-planar relationship;
  ii. and wherein, said first voltage potential is higher than said second voltage potential; and,
c. a continuous separating strip of polyvinylchloride, wherein said separating strip comprises a T-shaped dielectric having a first and a second arm and a leg, said leg disposed between and protruding from the first and second conducting surfaces, the leg having:
  i. a top horizontal surface having a width sufficiently wider than said width of said first and second conductive surfaces to promote the attraction and beading of water until the mass of a drop of water is sufficiently large to overcome the surface tension binding the drop to said top horizontal surface causing the drop to fall clear of said first and second conductive surfaces;
  ii. a vertical surface having a thickness and depending from the top horizontal surface and perpendicular thereto; and,
  iii. a bottom horizontal surface parallel to the top horizontal surface having said width; wherein said first and second arm have inside surfaces forming top and bottom bonding surfaces for the second and first conductive surfaces respectively.

5. A pest deterrent fence sold as a kit comprising at least:
a. a predetermined length of fence comprising:
  i. a first conductive surface to have a first voltage potential comprising a first panel having a width;
  ii. a second conductive surface to have a second voltage potential comprising a second panel having said width;
    wherein, said second conductive surface is to be placed adjacent to and above said first conductive surface in a co-planar relationship;
    and wherein, said first voltage potential is to be higher than said second voltage potential; and
  iii. a non-conductive separating strip of polyvinylchloride having a T-shape having a leg and first and second arms perpendicular to said leg forming said T-shape so that the leg of the T forms a dielectric disposed between and protruding from said first and second conductive surfaces and so that inside surfaces of said arms form bonding surfaces for said first and second conductive surfaces, said leg having a width sufficiently wider than said width of said first and second conductive surfaces to promote the attraction and beading of water until the mass of a drop of water is sufficiently large to overcome the surface tension binding the drop to said leg causing the drop to fall clear of said first and second conductive surfaces;
b. at least one container for containing a battery for energizing the first and second conductive surfaces, said container having a first and second electrode protruding there-from so as to mount the first and second conductive surfaces thereto, said first and second electrodes having electrical contact with the battery, the container further comprising a battery condition indicator and an on/off switch; wherein the container is mounted to a stake for implanting into the ground; and,
c. a plurality of supporting stakes for supporting said predetermined length of fence in a desired shape.

* * * * *